United States Patent [19]
Dunn et al.

[11] Patent Number: 4,931,812
[45] Date of Patent: Jun. 5, 1990

[54] FLOW CONTROL SYSTEM FOR INK CARTRIDGES

[75] Inventors: John B. R. Dunn; Lowell R. McDaniel, both of Corvallis; Patrick W. Shelley, Albany; Karen M. Lewey, Corvallis, all of Oreg.

[73] Assignee: Hewlett-Packard Company, Palo Alto, Calif.

[21] Appl. No.: 381,446

[22] Filed: Jul. 18, 1989

[51] Int. Cl.$^5$ .............................................. G01D 15/18
[52] U.S. Cl. ................................................ 346/140 A
[58] Field of Search ................................. 346/140 PD

[56] References Cited

U.S. PATENT DOCUMENTS

| | | | |
|---|---|---|---|
| 4,433,341 | 2/1984 | Thomas | 346/140 PD |
| 4,500,895 | 2/1985 | Buck et al. | 346/140 |
| 4,677,447 | 6/1987 | Nielsen | 346/140 |
| 4,714,937 | 12/1987 | Kaplinsky | 346/140 |
| 4,737,801 | 4/1988 | Ichihashi et al. | 346/140 PD |

OTHER PUBLICATIONS

Simpson, H. W., Drop-On-Demand Ink Jet Printing Head, Sep. 1981, vol. 24, No. 4, IBM Technical Disclosure Bulletin, p. 1820.
Hewlett-Packard Journal, May 1985, vol. 36, No. 5, pp. 1-27.

Primary Examiner—George H. Miller, Jr.

[57] ABSTRACT

An ink cartridge system is provided which includes a reservoir maintained at a negative pressure in communication with a printing system. As the printing system is activated, ink is expelled from the cartridge which draws ink from the reservoir by capillary action. To prevent the reverse flow of air and ink into the reservoir, a control unit is provided. The control unit includes an ink conduit communicating with a standpipe. A medial section is provided between the ink conduit and standpipe. The medial section includes an opening adapted to receive a ball within the ink conduit. The ball is freely movable within the ink conduit, but is larger than the opening. As a result, the outward flow of ink from the reservoir is allowed, while the backflow of ink and air into the reservoir is prevented by movement of the ball into the opening of the medial section.

20 Claims, 1 Drawing Sheet

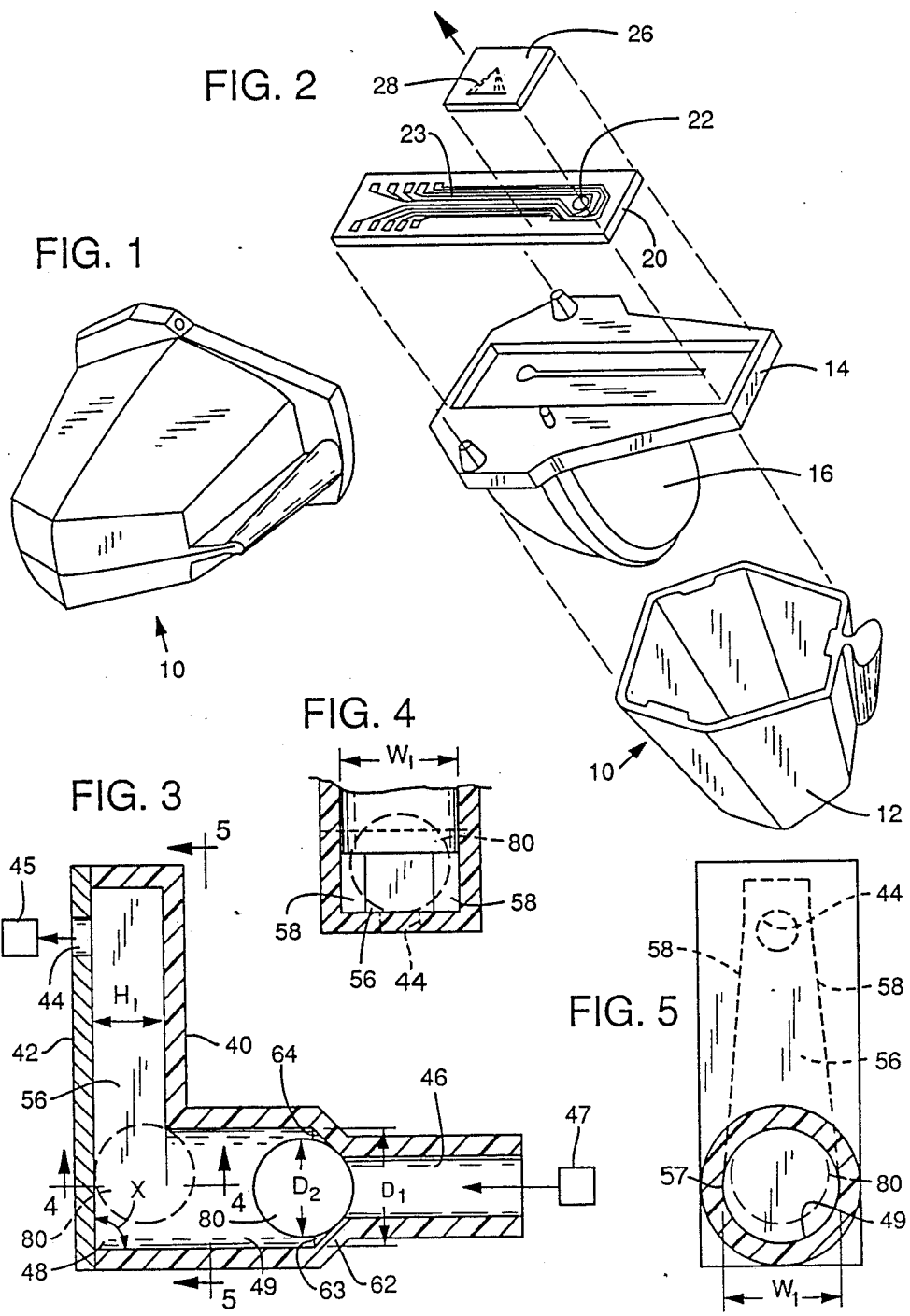

FLOW CONTROL SYSTEM FOR INK CARTRIDGES

BACKGROUND OF THE INVENTION

The present invention generally relates to ink cartridge printing systems, and more particularly to an ink cartridge having a control unit designed to prevent the reverse flow of ink and air into the cartridge reservoir.

The development of sophisticated ink jet printing systems has created a corresponding need for improved ink delivery cartridges. To satisfy this need, ink cartridges have been manufactured which include an ink reservoir in fluid communication with an orifice plate and resistor assembly. Activation of the resistor assembly generates heat which thermally excites the ink and expels it from the cartridge. This delivery procedure is known in the art, and described in the *Hewlett-Packard Journal*, May 1985, Vol. 36, No. 5. In addition, an exemplary cartridge using thermal ink excitation is illustrated in U.S. Pat. No. 4,500,895.

In the system described above, ink within the reservoir is normally maintained at a negative pressure. Ink is drawn out of the reservoir by capillary action which occurs when the ink is excited and expelled from the orifice plate. However, this type of system often experiences problems associated with the reverse flow of air and ink into the reservoir. This is caused by the negative pressure within the reservoir which draws air into the cartridge and pulls ink away from the orifice plate. When ink is displaced from the orifice plate, the printing process is interrupted, causing what is commonly known as a "deprime." In addition, the introduction of air into the cartridge and reservoir causes the ink therein to bubble or foam, thereby reducing the operating efficiency of the cartridge. Furthermore, any air in the reservoir will expand when ambient temperatures are increased. This expansion can force ink out of the reservoir and cartridge when not in use, causing uncontrolled leakage.

A variety of methods have been attempted to eliminate problems associated with the reverse flow of ink and air into ink cartridges. For example, a system exists in which a small screen is positioned in the cartridge between the ink reservoir and orifice plate. The surface tension of the ink and small mesh size of the screen minimize the reverse flow of air and ink into the reservoir. However, this technique is not entirely effective, and frequently causes the generation of air bubbles in the cartridge when the vacuum from the reservoir pulls air through the screen. As a result, the operating efficiency of the cartridge is reduced. A need therefore exists for an ink cartridge system having means for effectively controlling the reverse flow of air and ink into the system. The present invention satisfies this need in a manner not heretofore known in the art, as described below.

SUMMARY OF THE INVENTION

It is an object of the present invention to provide an ink cartridge system of improved efficiency and design.

It is another object of the invention to provide an ink cartridge system which delivers ink in a smooth, rapid and uniform manner.

It is another object of the invention to provide an ink cartridge system which requires minimal cleaning and maintenance.

It is a still further object of the invention to provide an ink cartridge system which uses a minimal number of operating components.

It is a still further object of the invention to provide an ink cartridge system which minimizes problems associated with the introduction of air into the cartridge.

It is an even further object of the invention to provide an ink cartridge system which minimizes problems associated with ink deprimes, thereby facilitating a smooth and uninterrupted flow of ink.

In accordance with the foregoing objects, an ink cartridge is provided which includes an ink reservoir maintained at a negative pressure in fluid communication with an ink delivery/printing system (e.g. heating resistor unit). As ink is expelled from the cartridge by the delivery system, fresh ink is drawn from the reservoir by capillary action. To prevent the reverse flow of air and ink into the reservoir, a special control unit is provided. The control unit is positioned within the cartridge between the reservoir and delivery/printing system, and includes at least one ink conduit communicating with an ink delivery standpipe. The standpipe is attached to the reservoir and draws ink therefrom. At the junction between the ink conduit and standpipe, a medial section is provided having an opening therethrough of progressively decreasing diameter. The medial section also has an annular, inwardly sloping interior wall surrounding the opening. The medial section is adapted to receive a free-floating spherical member (e.g. a ball) which resides within the ink conduit. The ball has a diameter greater than the opening in the medial section, and cannot pass therethrough. In operation, ink moves out of the reservoir, through the standpipe, and into the ink conduit for delivery from the cartridge. However, the reverse movement of air and ink into the reservoir is prevented by blockage of the opening in the medial section with the ball. Specifically, the ball is carried by the ink into the opening of the medial section, preventing the flow of ink and air therethrough. As a result, ink deprimes and the generation of air bubbles within the cartridges are controlled. Moreover, the ball is especially sensitive to directional changes in ink flow, since it is unencumbered and entirely free-floating.

These and other objects, features and advantages of the invention will be more fully described in the following brief description of the drawings and detailed description of a preferred embodiment presented below.

BRIEF DESCRIPTION OF THE DRAWINGS

FIG. 1 is a perspective view of an exemplary ink cartridge designed to incorporate the flow control unit of the present invention.

FIG. 2 is an exploded perspective view of the cartridge of FIG. 1.

FIG. 3 is a cross-sectional view of a flow control unit manufactured in accordance with the invention.

FIG. 4 is a view taken along lines 4—4 of FIG. 3.

FIG. 5 is a view taken along lines 5—5 of FIG. 3.

DETAILED DESCRIPTION OF A PREFERRED EMBODIMENT

The present invention involves an improved ink cartridge system which is characterized by a high degree of efficiency and minimal maintenance requirements.

An ink cartridge 10 usable in connection with the invention is illustrated in FIG. 1. This type of cartridge is manufactured by the Hewlett-Packard Company of Palo Alto, Calif. With reference to FIG. 2, the cartridge 10 includes a housing 12, backing plate 14, and bladder-like ink reservoir 16. Also included is a substrate 20 with an ink feed hole 22 and thin film resistor pattern 23 thereon. Secured to the substrate 20 as shown in FIG. 2 is an orifice plate 26 having drop expulsion holes 28 which communicate with the ink feed hole 22. Additional operating characteristics of this apparatus are presented in U.S. Pat. No. 4,500,895 which is incorporated by reference.

However, the invention as described herein is not limited to any specific type of ink cartridge or printing system. Instead, it may be used with any ink delivery/printing system having an ink reservoir maintained at a negative pressure.

With reference to FIGS. 3-5, a flow control unit 40 produced in accordance with the invention is illustrated. Control unit 40 includes an outer cover 42 and an ink feed orifice 44. The ink feed orifice 44 communicates with an ink printing/delivery system 45. The system 45 may take a variety of forms, including the resistor unit described above and discussed in U.S. Pat. No. 4,500,895.

If the control unit 40 is used in the cartridge 10 of FIGS. 1 and 2, the substrate 20 could function as the outer cover 42. Likewise, the ink feed orifice 44 could operate as the ink feed hole 22 described above.

The interior of the control unit 40 includes a first conduit 46 (commonly known is a standpipe) which is attached to an ink reservoir 47 maintained at a negative pressure. If the control unit 40 is used in the cartridge 10 of FIGS. 1 and 2, the reservoir 47 may consist of the bladder-like structure 16 shown in FIG. 2.

The control unit 40 also includes a second conduit 48 preferably consisting of a primary ink channel 49 which is circular in cross section as illustrated in FIG. 5, and having a diameter $D_1$ (FIG. 3). The primary ink channel 49 communicates with a secondary ink channel 56 shown in FIG. 3. In a preferred embodiment, the primary ink channel 49 is positioned at a angle "X" of about 90 degrees relative to the secondary ink channel 56 (FIG. 3.) With continued reference to FIG. 3, the secondary ink channel 56 has a height $H_1$. In a preferred embodiment, the secondary ink channel 56 has a maximum width $W_1$ at position 57 (FIGS. 4-5.) The secondary ink channel 56 progressively decreases in width from position 57 toward ink feed orifice 44 due to the use of inwardly sloping side walls 58 illustrated in FIGS. 4-5.

Positioned between the primary ink channel 49 and the standpipe 46 is a frustoconical medial section 62 illustrated in FIG. 3. The medial section 62 has an opening 63 with a diameter progressively decreasing in the direction of reservoir 47. The opening 63 is surrounded by an annular, inwardly sloping interior wall 64. The opening 63 progressively decreases in diameter due to the inwardly sloping configuration of the wall 64.

Positioned within the primary ink channel 49 is a spherical flow control member in the form of a ball 80. The ball 80 is preferably constructed of a material impervious to corrosion or reaction with ink. The ball 80 may be manufactured of a variety of materials including polypropylene plastic. It has a diameter $D_2$ which is less than the diameter $D_1$ of the primary ink channel 49. As a result, the ball 80 may freely move within the primary ink channel 49 (FIG. 3). Free, unencumbered movement of the ball 80 within the primary ink channel 49 is important. Accordingly, the primary ink channel 49 should be sufficiently large to allow the free movement of ball 80 therein whether the channel 49 is circular in cross section or not.

With respect to the secondary ink channel 56, the diameter $D_2$ of the ball 80 is less than the width $W_1$ (FIG. 4), but greater than the height $H_1$ (FIG. 3) of the secondary ink channel 56. This design prevents the ball 80 from passing out of the primary ink channel 49 into the secondary ink channel 56, as shown in dashed lines in FIG. 3. However, ink is allowed to pass between channel 49 and channel 56 because the diameter $D_2$ of the ball 80 is less than the width $W_1$ of the secondary ink channel 56, as previously described and illustrated in FIG. 4.

In addition, the ball 80 is larger than the opening 63 as shown in FIG. 3. This design prevents the ball 80 from passing through the medial section 62 into the standpipe 46, as described in greater detail below.

In operation, ink is expelled from the cartridge using the printing/delivery system 45 which may take a variety of forms, as described above. As a result, ink flows by capillary action out of the reservoir 47 through the standpipe 46, medial section 62, primary ink channel 49, and secondary ink channel 56 prior to ejection. The ball 80 remains free-floating within the primary ink channel 49 due to the dimensional differences between the ball 80 and the primary ink channel 49 as previously described. As ink is delivered, the ball 80 assumes the position shown in dashed lines in FIG. 3. However, if the negative pressure within the reservoir 47 causes air to enter the cartridge, ink will be displaced from the printing/delivery system. As a result, ink and air will begin moving in a reverse direction toward the reservoir 47. When this occurs, the ball 80 is moved by the ink toward and into the medial section 62. Since the ball 80 is larger than the opening 63 in the medial section 62, it will engage the wall 64 surrounding the opening 63 as shown in solid lines in FIG. 3. As a result, ink and air are prevented from flowing rearwardly into the standpipe 46 and reservoir 47, thereby minimizing the introduction of air into the reservoir and controlling deprimes.

Use of the control unit 40 as described herein represents an important advance in the art of ink delivery. It offers superior results compared with the screen systems previously discussed. Moreover, the use of a free-floating, unencumbered ball 80 enables the ball 80 to be extremely responsive to minute directional changes in ink flow. As a result, the control unit 40 operates instantaneously, and offers minimal resistance to the outward flow of ink in comparison with other flow control systems.

Having herein described a preferred embodiment of the invention, it is anticipated that suitable modifications may be made thereto by individuals skilled in the art. Accordingly, the invention shall only be construed in connection with the following claims:

We claim:

1. A flow control unit for use in an ink cartridge having a reservoir maintained at a negative pressure in combination with printing means for withdrawing ink from said reservoir comprising:

a first conduit in fluid communication with said reservoir;

a second conduit positioned between and in fluid communication with said first conduit and said printing means;

a medial section positioned between said first conduit and said second conduit, said medial section comprising an opening therethrough; and a spherical ink flow control member positioned within said second conduit and having a diameter greater than that of said opening in said medial section, said second conduit being sufficiently large to allow the free movement of said control member therein, said control member allowing ink to flow outwardly from said reservoir through said first conduit, medial section, and second conduit to said printing means, while preventing the reverse flow of air and ink into said cartridge and reservoir by blocking said opening in said medial section.

2. The control unit of claim 1 wherein said opening in said medial section has a progressively decreasing diameter.

3. The control unit of claim 1 wherein said second conduit comprises a primary ink channel and a secondary ink channel in fluid communication with each other, said spherical ink flow control member residing within said primary ink channel.

4. The control unit of claim 3 wherein said primary ink channel is positioned at a 90 degree angle relative to said secondary ink channel.

5. The control unit of claim 3 wherein said secondary ink channel has a height which is less than said diameter of said spherical ink flow control member, and a width which is greater than said diameter of said control member.

6. The control unit of claim 1 wherein said spherical ink flow control member is comprised of plastic.

7. The control unit of claim 1 wherein said medial section further comprises an annular, inwardly angled interior wall surrounding said opening, said spherical ink flow control member being adapted to engage said wall and block said opening in order to prevent said reverse flow of said air and ink into said cartridge and reservoir.

8. A flow control unit for use in an ink cartridge having a reservoir maintained at a negative pressure in combination with printing means for withdrawing ink from said reservoir comprising:

a first conduit in fluid communication with said reservoir;

a second conduit positioned between and in fluid communication with said first conduit and said printing means, said second conduit comprising a primary ink channel and secondary ink channel in fluid communication with each other;

a medial section positioned between said primary ink channel and said first conduit, said medial section comprising an opening therethrough of progressively decreasing diameter, and an annular, inwardly angled interior wall surrounding said opening; and a spherical ink flow control member positioned within said primary ink channel of said second conduit and having a diameter greater than that of said opening in said medial section, said primary ink channel being sufficiently large to allow the free movement of said control member therein, said secondary ink channel of said second conduit having a height which is less than said diameter of said control member and a width which is greater than said diameter of said control member, said control member allowing ink to flow outwardly from said reservoir through said first conduit, medial section, and said second conduit to said printing means, while preventing the reverse flow of air and ink into said cartridge and reservoir by engaging said wall of said medial section and blocking said opening therethrough.

9. The control unit of claim 8 wherein said spherical ink flow control member is comprised of plastic.

10. The control unit of claim 8 wherein said primary ink channel is positioned at a 90 degree angle relative to said secondary ink channel.

11. An ink cartridge comprising:
a reservoir maintained at a negative pressure;
printing means for withdrawing ink from said reservoir; and
a flow control unit operatively connected to and between said reservoir and said printing means, said control unit comprising:
a first conduit in fluid communication with said reservoir;
a second conduit positioned between and in fluid communication with said first conduit and said printing means;
a medial section positioned between said first conduit and said second conduit, said medial section comprising an opening therethrough; and
a spherical ink flow control member positioned within said second conduit and having a diameter greater than that of said opening in said medial section, said second conduit being sufficiently large to allow the free movement of said control member therein, said control member allowing ink to flow outwardly from said reservoir through said first conduit, medial section, and said second conduit to said printing means, while preventing the reverse flow of air and ink into said cartridge and reservoir by blocking said opening in said medial section.

12. The cartridge of claim 11 wherein said opening in said medial section of said control unit has a progressively decreasing diameter.

13. The cartridge of claim 11 wherein said second conduit of said control unit comprises a primary ink channel and a secondary ink channel in fluid communication with each other, said spherical ink flow control member residing within said primary ink channel.

14. The cartridge of claim 13 wherein said primary ink channel of said control unit is positioned at a 90 degree angle relative to said secondary ink channel.

15. The cartridge of claim 13 wherein said secondary ink channel of said control unit has a height which is less than said diameter of said spherical ink flow control member, and a width which is greater than said diameter of said control member.

16. The cartridge of claim 11 wherein said spherical ink flow control member is comprised of plastic.

17. The cartridge of claim 11 wherein said medial section of said control unit further comprises an annular, inwardly angled interior wall surrounding said opening, said spherical ink flow control member being adapted to engage said wall and block said opening in order to prevent said reverse flow of said air and ink into said cartridge and reservoir.

18. An ink cartridge comprising:
a reservoir maintained at a negative pressure;
printing means for withdrawing ink from said reservoir; and
a flow control unit operatively connected to and between said reservoir and said printing means, said control unit comprising:

a first conduit in fluid communication with said reservoir;

a second conduit positioned between and in fluid communication with said first conduit and said printing means, said second conduit comprising a primary ink channel and secondary ink channel in fluid communication with each other;

a medial section positioned between said primary ink channel and said first conduit, said medial section having an opening therethrough of progressively decreasing diameter, and an annular, inwardly angled interior wall surrounding said opening; and a spherical ink flow control member positioned within said primary ink channel of said of second conduit and having a diameter greater than that of said opening in said medial section, said primary ink channel being sufficiently large to allow the free movement of said control member therein, said secondary ink channel of said second conduit having a height which is less than said diameter of said control member and a width which is greater than said diameter of said control member, said control member allowing ink to flow outwardly from said reservoir through said first conduit, medial section, and said second conduit to said printing means, while preventing the reverse flow of air and ink into said cartridge and reservoir by engaging said wall of said medial section and blocking said opening therethrough.

19. The cartridge of claim 18 wherein said spherical ink flow control member is comprised of plastic.

20. The cartridge of claim 18 wherein said primary ink channel of said control unit is positioned at a 90 degree angle relative to said secondary ink channel.

* * * * *